United States Patent [19]
Dalton et al.

[11] Patent Number: 5,856,350
[45] Date of Patent: Jan. 5, 1999

[54] 3-PHENYL-1,4-DIALKYL-1,2,4-TRIAZOLIUM SALTS AND THEIR USE AS ANTIDEPRESSANTS

[75] Inventors: Christopher Robin Dalton; John Michael Kane; John Herr Kehne, all of Cincinnati, Ohio

[73] Assignee: Hoechst Marion Roussel, Inc., Cincinnati, Ohio

[21] Appl. No.: 764,964

[22] Filed: Dec. 13, 1996

Related U.S. Application Data

[63] Continuation of Ser. No. 426,744, Apr. 20, 1995, abandoned.
[51] Int. Cl.$^6$ ........................ A01N 43/653; C07D 249/08
[52] U.S. Cl. .................. 514/383; 548/267.8; 548/268.6; 548/269.4
[58] Field of Search ........................ 514/383; 548/267.8, 548/268.6, 269.4

[56] References Cited

U.S. PATENT DOCUMENTS

| | | | |
|---|---|---|---|
| 4,230,715 | 10/1980 | Albrecht et al. | 424/269 |
| 4,414,221 | 11/1983 | Parsons et al. | 424/269 |
| 4,775,688 | 10/1988 | Kane et al. | 514/384 |
| 4,847,276 | 7/1989 | Yarrington | 514/384 |
| 4,946,856 | 8/1990 | Kane et al. | 514/384 |
| 4,966,909 | 10/1990 | Kane et al. | 514/359 |
| 4,981,863 | 1/1991 | Kane et al. | 514/384 |
| 5,143,933 | 9/1992 | Kane et al. | 514/384 |
| 5,158,968 | 10/1992 | Kehne et al. | 514/384 |
| 5,331,002 | 7/1994 | Miller | 514/384 |
| 5,386,062 | 1/1995 | Teles et al. | 568/463 |
| 5,436,252 | 7/1995 | Sorensen et al. | 514/309 |

FOREIGN PATENT DOCUMENTS

| | | |
|---|---|---|
| 1481761 | 6/1966 | France . |
| 3314659 | 12/1983 | Germany . |
| 50-63119 | 5/1975 | Japan . |

OTHER PUBLICATIONS

M. Y. Mhassalkar, et al., Further Studies in substituted 4H–1,2,4–Triazoles for Possible Hypoglycemic Activity, *J. Med. Chem.* 14, No. 3, 260–2 (1971).
Becker, et al., J. prakt. Chem. 330 (3), 325–337 (1988).
Alberti, et al., Ann. Chim. (Rome) 65(5–6), 305–314 (1975).

*Primary Examiner*—Patricia L. Morris
*Attorney, Agent, or Firm*—Edlyn S. Simmons

[57] ABSTRACT

This invention relates to the treatment of depression by administration of novel 3-($R_n$-phenyl)-1,4-dialkyl-1,2,4-triazolium salts of the formula

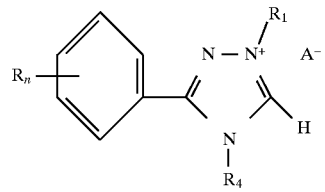

wherein
  R is halogen, trifluoromethyl, $C_{1-4}$ lower alkyl or $C_{1-4}$ lower alkoxy,
  n is zero, 1 or 2, and
  $R_1$ and $R_4$ independently represent $C_{1-3}$ lower alkyl;
  and $A^-$ represents a pharmaceutically acceptable anion.

45 Claims, No Drawings

3-PHENYL-1,4-DIALKYL-1,2,4-TRIAZOLIUM SALTS AND THEIR USE AS ANTIDEPRESSANTS

This is a continuation of U.S. Ser. No. 08/426,744, filed Apr. 20, 1995, now abandoned.

This invention relates to novel 3-phenyl-1,4-dialkyl-1,2,4-triazolium salts and to their use as antidepressants.

More specifically, this invention relates to novel triazolium salts of the formula I and to their use as pharmaceutical agents for treatment of depression.

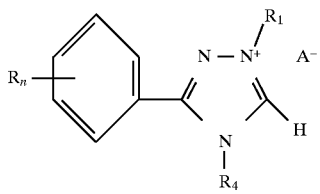

wherein
R represents halogen, trifluoromethyl, $C_{1-4}$ lower alkyl and $C_{1-4}$ lower alkoxy;
n represents 0, 1 or 2;
$R_1$ and $R_4$ independently represent $C_{1-3}$ lower alkyl; and
A represents a pharmaceutically acceptable anion.

BACKGROUND OF THE INVENTION

3- And 5-aryl triazole derivatives have been reported in the prior art to have a wide variety of pharmacological activities. 5-Aryl-2,4-dialkyl-3H-1,2,4-triazole-3-thiones, for example, are known to have activity against depression, as claimed in U.S. Pat. No. 4,775,688, and U.S. Pat. No. 4,775,689, against thrombocytosis, as claimed in U.S. Pat. No. 4,847,276, against the symptoms of Wernicke-Korsakoff syndrome, as claimed in U.S. Pat. No. 5,100,906, against Alzheimer's disease, as claimed in U.S. Pat. No. 5,236,942,and in enhancement of memory and cognition, as claimed in U.S. Pat. No. 5,331,002. The use of 5-phenyl-1,2,4-triazole-3-thione as an antisecretory agent is disclosed U.S. Pat. No. 4,230,715. 5-Aryl-1,2,4-triazol-3-one derivatives are known to have activity against seizure disorders, as claimed in U.S. Pat. No. 4,966,909, and U.S. Pat. No. 4,946,856, and for treatment of neurodegeneration due to stroke, as claimed in pending U.S. Ser. No. 494,049. 3-Phenyl-3-alkylthio, alkenylthio, alkoxy and hydroxy-triazole derivatives are described as anticoccidial agents in Japanese Kokai 50-63119. 3-Aryl-5-alkylthio-, alkylsulfinyl- and alkylsulfonyl-4H-1,2,4-triazole derivatives are known to have activity against convulsant seizures, as claimed in U.S. Pat. No. 5,143,933, against anxiety, as claimed in U.S. Pat. No. 4,981,863, against muscle spasms and muscle tension, as claimed in U.S. Pat. No. 4,900,743, and against hyperreflexia due to spinal trauma, as claimed in U.S. Pat. No. 5,158,968. Mhasalkar, et al. (J. Med. Chem 14(3), 260–262 (1971)) evaluated a series of 3-phenyltriazoles for hypoglycemic activity and noted that the level of activity varied substantially when the substituents on the 4- and 5-positions of the triazole ring and on the benzene ring were changed.

By contrast, 3-aryltriazolium salts known to the prior art are not reported to have beneficial pharmacological activity. For example, triazolium dyes are described in German Offenlegung 3,314,659, assigned to VEB Filfabrik Wolfen, and in an article by Alberti (Ann. Chim. (Rome) (1975), 65(5–6), 305–14). Fr. 1,481,761, assigned to Badische Anilin, describes triazolium salts useful as plant protection agents. U.S. Pat. No. 4,414,221, assigned to FBC Ltd., includes triazolium salts in a genus of o-halophenyl-substituted N-heterocyclic compounds useful as pesticides against acarids and insects.

DETAILED DESCRIPTION OF THE INVENTION

3-Phenyltriazolium salts of formula I have been found to display activity as antidepressants without showing other activities characteristic of known 3-or 5-aryltriazole derivatives. The 3-(3-fluorophenyl)-1,4-dimethyl-1,2,4-triazolium ion has been identified in the urine of test animals as a metabolite of 5-(3-fluorophenyl)-2,4-dimethyl-3H-1,2,4-triazole-3-thione, a compound known to antidepressant activity as well as activity in tests indicative of protection from neurodegeneration resulting in the symptoms of Wernicke-Korsakoff syndrome and Alzheimer's disease. However, a 3-(3-fluorophenyl)-1,4-triazolium salt has been found in pharmacological tests to show selective activity against depression without concommitant activity against neurodegeneration or activity in tests for other pharmacological effects of related triazole derivatives.

In formula I, the phenyl moiety may be unsubstituted or a mono-substituted phenyl moiety wherein n is 1 with the substitutent group R located at any of the ortho, meta or para positions, or a disubstituted phenyl moiety wherein n is 2 and the substituent groups may be the same or different and may be attached in any of the 2,3-; 2,4-; 2,5-; 2,6-; 3,4-; and 3,5-positions. As used herein, halogen represents chloro, fluoro bromo or iodo. When the phenyl ring is substituted by $C_{1-4}$ alkyl or $C_{1-4}$ alkoxy, the alkyl moiety may be straight or branched. When the phenyl ring is substituted, the substituent group is preferably halogen, with fluoro being most preferred. Preferably $R_1$ and $R_4$ represent methyl, but may independently represent any straight or branched $C_{1-3}$ alkyl group.

For convenience, formula I has been drawn herein with the positive charge localized at the nitrogen atom in the 1-position of the triazole ring. It is well known, however, that in a ring system such as the 1,4-dialkyl-1,2,4-triazolium system of formula I, the positive charge is not localized at a particular nitrogen atom, but is dispersed over the conjugated ring system. Formula I is not to be interpreted as limited to compounds charged at the 1-nitrogen atom. Rather, formula I encompasses all compounds having the defined skeleton and substituent groups and having a positive charge, whether the charge is localized at one of nitrogen or carbon atoms of the ring skeleton or delocalized around the ring system.

The antidepressant properties of the claimed compounds and their relative potencies may readily be determined using standard laboratory methodology. When compared with other agents clinically known to be useful as antidepressants, the dosage regimen may readily be ascertained by those of ordinary skill in the art.

For example, antidepressant activity is indicated by the assay testing for prevention of reserpine-induced ptosis in mice. In this assay, test groups of weighed mice are housed individually in wire mesh cages and administered test compound or vehicle. At a selected time thereafter, reserpine is administered as a 0.2 mg/ml solution in dilute acetic acid at a dose of 2 mg/kg intravenously into a tail vein. In each assay the animals are examined individually in a Plexiglas® cylinder 90 minutes later. Prevention or delay in ptosis is considered significant if the average closure of both eyes is less than 50% after observing for 30 seconds. The $ED_{50}$ for prevention of ptosis is defined as the dose of test compound that significantly prevents ptosis in 50% of the test animals.

In these tests imipramine has an $ED_{50}$ of 4.89 mg/kg (using a 60 minute pre-treatment time) while 3-(4-chlorophenyl)-1,4-dimethyl-1,2,4-triazolium hydrosulfate, the most active compound of formula I tested, has an $ED_{50}$ of 0.09 mg/kg under the same conditions.

Another assay utilized to evaluate antidepressant activity is testing for the antagonism to Ro 4-1284*—induced hypothermia. (*Niemegeers, Carlos, J. E. "Antagonism of Reserpine—Like Activity", edited by S. Fielding and Lal, published by Futura, pg. 73–98.) In this test, groups of male mice are weighed and housed individually in wire mesh cages. The rectal temperature of each mouse is recorded and the test compound or vehicle is then administered. At a selected time thereafter, Ro 4-1284, prepared as a 2 mg/ml solution in distilled water, is administered at a dose of 20 mg/kg i.p. Mice are then placed in a cold room (36° F.) for 30 minutes, and then returned to room temperature for 30 minutes. At this time (60 minutes after Ro 4-1284 administration) the rectal temperature of each mouse is again recorded. Under these conditions, Ro 4-1284 causes a fall in rectal temperature of 10° to 12° C. The final temperatures of control groups of ten Ro 4-1284-treated mice from a number of experiments are combined to form an "historic control" of 100 mice. This control is updated periodically by replacement of the oldest data. Any drug-treated animal which has a final temperature (after Ro 4-1284) which is greater than the mean ±2 S.D. of the Ro 4-1284 historic control is considered to exhibit significant antagonism to the hypothermic effect of Ro 4-1284. The $ED_{50}$ for antagonism is defined as that dose of test compound which significantly antagonizes Ro 4-1284 hypothermia in 50% of the test animals.

Using a 60 minute pre-treatment time and these criteria for evaluation of effects, desipramine was found to have an $ED_{50}$ of 0.1 mg/kg i.p.; imipramine, an $ED_{50}$ of 1.8 mg/kg i.p., catron, an $ED_{50}$ of 0.7 mg/kg i.p., and 3-(3-fluorophenyl)-1,4-dimethyl-1,2,4-triazolium hydrosulfate the most active compound of formula I tested, an $ED_{50}$ of 0.34 mg/kg i.p.

The results of testing a number of compounds of formula I for the effects summarized above, as well as their $LD_{50}$, are summarized in Table I.

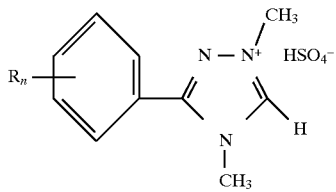

| $R_n$ | Reserpine-Induced Ptosis $ED_{50}$, mg/kg | Ro 4-1284 Induced Hypothermia $ED_{50}$, mg/kg | $LD_{50}$ mg/kg |
|---|---|---|---|
| 4-Br— | 0.23 | 0.81 | >200<400 |
| 4-Cl— | 0.09 | 0.51 | >100<200 |
| 4-I— | 2.82 | >6.25 | >100<200 |
| 2-F— | 0.28 | 0.74* 0.58 | >100<200 |
| 3-F— | 0.19 | 0.34 | >200<400 |
| 2,6-F$_2$— | 5.34 | 0.58 | >100<200 |
| 3-F-2-CH$_3$O— | 1.31 | 2.0 | >100<200 |
| 2-CH$_3$O— | >12.5 | >3.12 | >50<100 |

*Two determinations were made and are listed separately.

In common with other compounds showing activity in the foregoing assays, the compounds of this invention have pharmacological effects generally attributed to antidepressants and thus the compounds of this invention will elevate mood in patients suffering from depression and will therefore have an end-use application of treating patients suffering from endogenous depression, a term used interchangeably with psychotic or involutional depression. In this use, the compound (I) will exert a relatively quick onset of action and have a prolonged duration of activity. In general, the compounds are expected to exert their anti-depressant effects at dose levels of about 0.25–25 mg/kg of body weight per day although, of course, the degree of severity of the disease state, age of the patient and such other factors determined by the attending diagnostician will influence the exact course and dosage regimen suitable for each patient. In general, the parenterally administered doses are about ¼ to ½ that of the orally administered dose.

For oral administration, the compounds can be formulated into solid or liquid preparations such as capsules, pills, tablets, troches, powders, solutions, suspensions or emulsions. The solid unit dosage forms can be a capsule which can be of the ordinary gelatin type containing, for example, lubricants and inert filler, such as lactose, sucrose or cornstarch. In another embodiment, the compounds of general formula I can be tableted with conventional tablet bases such as lactose, sucrose and cornstarch, in combination with binders, such as acacia, cornstarch or gelatin, disintegrating agents such as potato starch or alginic acid, and a lubricant such as stearic acid or magnesium stearate.

For parenteral administration, the compounds may be administered as injectable dosages of a solution or suspension of the compound in a physiologically acceptable diluent with a pharmaceutical carrier which can be a sterile liquid such as water, alcohols, oils and other acceptable organic solvents, with or without the addition of a surfactant and other pharmaceutically acceptable adjuvants. Illustrative of oils which can be employed in these preparations are those of petroleum, animal, vegetable, or synthetic origin, for example, peanut oil, soybean oil and mineral oil. In general, water, saline, aqueous dextrose and related sugar solutions, ethanol and glycols such as propylene glycol or polyethylene glycol, or 2-pyrrolidone are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert material such as biodegradable polymers or synthetic silicones, for example Silastic®, a silicone rubber manufactured by the Dow-Corning Corporation.

As is true in many classes of compounds generally suitable for any particular pharmacological activity having a therapeutic end-use application, certain subgeneric groups and certain specific members of the class are preferred because of their overall therapeutic index and their biochemical and pharmacological profile. In this instance the preferred compounds are those wherein both $R_1$ and $R_4$ groups are methyl, and those wherein the R substituent is fluoro or chloro. Compounds wherein the anion $A^-$ is the hydrosulfate anion are also preferred. Specifically preferred compounds are 3-(3-fluorophenyl)-1,4-dimethyl-1,2,4-triazolium hydrosulfate and 3-(4-chlorophenyl)-1,4-dimethyl-1,2,4-triazolium hydrosulfate.

The compounds of formula I may readily be prepared using processes and procedures analogously known in the art as seen by the following reaction scheme.

REACTION SCHEME

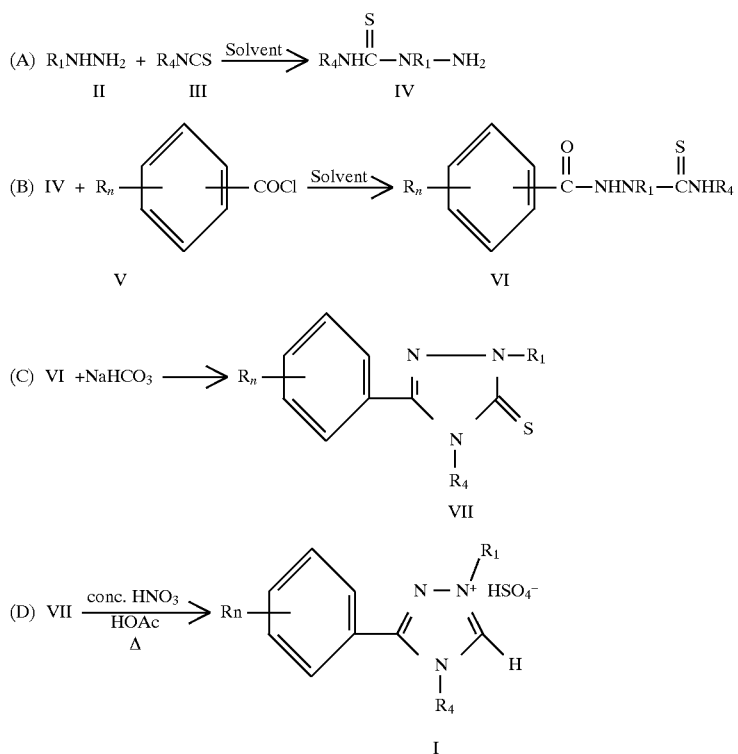

wherein $R_1$, $R_4$, n and R are as previously defined.

In step A, the preparation of the thiosemicarbazides (IV) is readily effected by reacting hydrazine (II) with an isothiocyanate (III) by contacting the reactants in a suitable solvent. The reaction is quite rapid and may be carried out at 0° C. to room temperature. Although the reaction proceeds rapidly, the mixture may be left for up to 24 hours without significant decrease in yields. Reflux conditions may be employed but are not preferred. Almost all solvents (with the exception of water and organic acids) may be used. Anhydrous alcohols (preferably ethanol or methanol) are preferred although dimethylformamide (DMF), $CHCl_3$, $CH_2Cl_2$, tetrahydrofuran (THF) and $Et_2O$ may also be used. The required hydrazines and isothiocyanates are usually commercially available, but may be prepared by known techniques.

In Step B, the desired substituted benzoyl thiosemicarbazides (VI) may be prepared by reacting the thiosemicarbazides (IV) with an $R_n$-substituted benzoyl chloride (V) in an aprotic solvent such as pyridine, $CHCl_3$, THF or the like. The acylation proceeds rather easily at temperatures ranging from 0°C. to room temperature over periods of 3 to 24 hours, although elevated temperatures (e.g. reflux temperatures) may be employed. Again, the acid halides (V) generally are commercially available but may also be prepared from the corresponding acids which are generally commercially available.

In Step C, the substituted benzoyl thiosemicarbazides (VI) are subjected to a cyclization reaction which is effected by heating the compounds (VI) in an aqueous base, e.g. sodium bicarbonate or sodium hydroxide. Alcoholic bases may be utilized, but generally are less desirable. The reaction is conducted at about the reflux temperature of the solvent, preferably at about 65°–100° C. In practice, the thiosemicarbazides (VI) need not be purified for use in Step C so that even 1:1 mixtures with pyridine hydrochloride, produced as a by-product when pyridine is employed as a solvent in Step B, may be used.

In step D, the triazole thione (VII) is suspended in acetic acid and a solution of 6–10 equivalents of nitric acid in acetic acid is added. The reaction mixture becomes a black solution and immediately gives off $NO_2$ gas. The mixture is refluxed for 10–60 minutes, cooled slightly, and poured into ether with stirring. After being stirred for 1–6 hours, the resulting crystalline triazolium hydrosulfate salt of formula I is filtered off under suction, washed with ether or another organic liquid in which the triazolium salt is insoluble, and dried, preferably under high vacuum. Hydrosulfate salts of formula I prepared by this method are analytically pure without the need for recrystallization.

Alternatively, the triazolethiones of formula VII may be dissolved in glacial acetic and reacted with $HBF_4$ and hydrogen peroxide according to the general method of H. G. O. Becker, et al. (J. prakt. Chem. 330 (3), 325–337 (1988)) to form a triazolium tetrafluoroborate salt of formula I.

Hydrosulfate salts of formula I are particularly suitable for pharmaceutical administration. Triazolium derivatives of formula I may also be administered as salts wherein $A^-$ is any other pharmaceutically acceptable anion, with the chloride salt being particularly suitable. Salts where $A^-$ is a pharmaceutically acceptable anion other than hydrosulfate of tetrafluoroborate may be readily prepared by using known anion exchange techniques.

The following specific examples are given to illustrate the preparation of the compounds of this invention although the scope of compounds exemplified is not meant to be limiting.

Preparation of $R_1,R_4$-Substituted-Thiosemicarbazides

EXAMPLE 1

2,4-Dimethylthiosemicarbazide

To a stirred solution of methyl hydrazine (16.0 ml, 3.00× $10^{-1}$ mole) and sieve dry ethanol (50 ml) was added dropwise a solution of methyl isothiocyanate (22.0 g, 3.00×$10^{-1}$ mole) and sieve dry ethanol (30 ml). The reaction was exothermic and gently refluxed as the isothiocyanate was added. A precipitate soon formed. After stirring overnight, the reaction was cooled in an ice bath. The precipitate was then collected by filtration, washed with a little cold isopropanol, and dried by suction, affording a colorless solid: 26.7 g (75%). This material was crystallized two times from water and two times from isopropanol, affording small colorless needles; 14.7 g (41%), mp 135°–137° C.

Preparation of 1-($R_n$-Benzoyl)-$R_1$, $R_4$, -Substituted Thiosemicarbazides

EXAMPLE 2

2,4-Dimethyl-1-(3-fluorobenzoyl)thiosemicarbazide

To a stirred, room temperature, solution of 2,4-dimethylthiosemicarbazide (5.96 g, 50.0 mmol) and dry pyridine (100 mL) was added dropwise 3-fluorobenzoyl chloride (7.93 g, 50.0 mmol). After stirring overnight, the reaction mixture was evaporated at reduced pressure. The concentrate was slurried with water and that which did not dissolve was collected by filtration. Crystallization of this material from ethanol afforded the desired product as colorless needles, mp 202°–205° C.

Preparation of Intermediate Triazole-3-thiones

EXAMPLE 3

2,4-Dihydro-2,4-dimethyl-5-(3-fluorophenyl)-3H-1,2,4-triazole-3-thione 2,4-Dimethyl-1-(3-fluorobenzoyl)thiosemicarbazide (11.1 g, 46.0 mmol) and 1 molar aqueous sodium bicarbonate (460 mL, 0.460 mol) were stirred and heated to reflux. After being refluxed for 5 h, the reaction was allowed to cool to room temperature. After stirring overnight, the reaction was placed in the freezer for several hours. The precipitate was then collected by filtration. Crystallization from isopropanol afforded the desired product as colorless, matted needles, mp 126°–128° C.

In a similar manner, by substituting a variety of substituted benzoyl chlorides and a variety of 4-substituted thiosemicarbazides for the reactants of examples 1–3 and by substantially following the techniques therein, the following compounds are readily prepared.

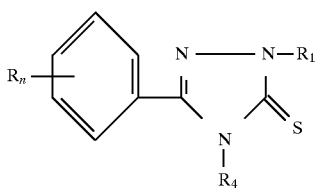

I

| $R_n$ | $R_1$ | $R_4$ | M.P. °C. |
|---|---|---|---|
| 4-F | $CH_3$ | $CH_3$ | 130–132° |
| 2-F | $CH_3$ | $CH_3$ | 106–108° |
| 3-F | $CH_3$ | $CH_3$ | 126–128° |
| 2,4-$F_2$ | $CH_3$ | $CH_3$ | 102–104° |
| 2,6-$F_2$ | $CH_3$ | $CH_3$ | 158–160° |
| 4-Br | $CH_3$ | $CH_3$ | 145–146° |
| 4-I | $CH_3$ | $CH_3$ | 183–185° |
| 4-Cl | $CH_3$ | $C_2H_5$ | 113–115° |
| 4-Cl | $C_2H_5$ | $CH_3$ | 118–120° |
| 4-Cl | $C_2H_5$ | $C_2H_5$ | 91–93° |
| 2-Cl | $CH_3$ | $CH_3$ | 138–140° |
| 4-Cl | $CH_3$ | $CH_3$ | 114–116° |
| 4-Cl | $CH_3$ | $n$-$C_3H_7$ | B.P. 240–250° 0.55 mm Hg |
| 2,4-$Cl_2$ | $CH_3$ | $CH_3$ | 135–137° |
| 3,4-$Cl_2$ | $CH_3$ | $CH_3$ | 161–163° |
| 2,6-$Cl_2$ | $CH_3$ | $CH_3$ | 115–116° |
| — | $CH_3$ | $CH_3$ | 134–135° |
| — | $C_2H_5$ | $CH_3$ | 105–107° |
| — | $CH_3$ | $C_2H_5$ | B.P. 388 746 mm Hg |
| 4-$CH_3$ | $CH_3$ | $CH_3$ | 94–96° |
| 4-t-$C_4H_9$ | $CH_3$ | $CH_3$ | 160–162° |
| 2-$CH_3O$ | $CH_3$ | $CH_3$ | 110–112° |
| 4-$CH_3O$ | $CH_3$ | $CH_3$ | 96–98° |
| 2-$C_4H_9O$, 3 $CH_3O$ | $CH_3$ | $CH_3$ | 95–97° |
| 3-$CF_3$ | $CH_3$ | $CH_3$ | 73–75° |

Preparation of 3-Phenyl-1,4-dialkyltriazolium Salts

EXAMPLE 4

3-(3-Fluorophenyl)-1,4-dimethyl-1,2,4-triazolium hydrosulfate 2,4-Dihydro-2,4-dimethyl-5-(3-fluorophenyl)-3H-1,2,4-triazole-3-thione (3.00 g, 13.4 mmol was suspended in glacial acetic acid (5 mL). The suspension was stirred and a solution of concentrated nitric acid (7.25 g, 81 mmol) and glacial acetic acid (25 mL) was added in one portion. The reaction was heated to reflux. After being refluxed for 20 min, the reaction was allowed to cool at which time it was poured into stirred anhydrous ether (600 mL). The resulting yellowish oil crystallized and after 2 h the desired product was isolated by filtration as yellowish green crystals, mp 106°–107° C.

In a similar manner, by substituting an appropriate intermediate triazole-3-thione in the procedure of Example 4, the following compounds are readily prepared.

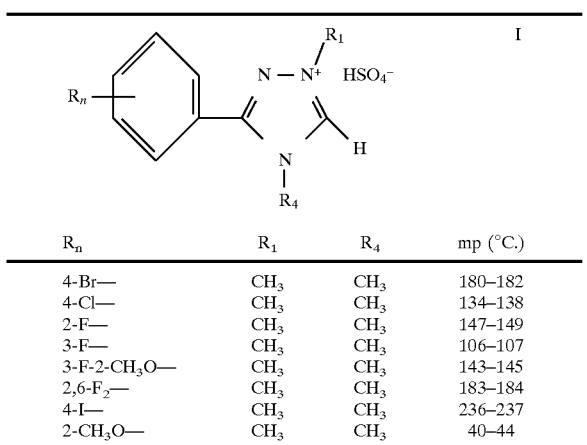

| $R_n$ | $R_1$ | $R_4$ | mp (°C.) |
|---|---|---|---|
| 4-Br— | $CH_3$ | $CH_3$ | 180–182 |
| 4-Cl— | $CH_3$ | $CH_3$ | 134–138 |
| 2-F— | $CH_3$ | $CH_3$ | 147–149 |
| 3-F— | $CH_3$ | $CH_3$ | 106–107 |
| 3-F-2-$CH_3$O— | $CH_3$ | $CH_3$ | 143–145 |
| 2,6-$F_2$— | $CH_3$ | $CH_3$ | 183–184 |
| 4-I— | $CH_3$ | $CH_3$ | 236–237 |
| 2-$CH_3$O— | $CH_3$ | $CH_3$ | 40–44 |

What is claimed is:

1. A compound of the formula

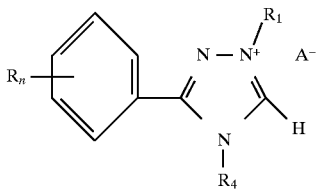

wherein

R is halogen, trifluoromethyl, $C_{1-4}$ lower alkyl or $C_{1-4}$ lower alkoxy;

n is zero, 1 or 2;

$R_1$ and $R_4$ independently represent $C_{1-3}$ lower alkyl;

and $A^-$ represents a pharmaceutically acceptable anion.

2. A compound of claim 1 wherein R is halogen.
3. A compound of claim 2 wherein R is fluoro.
4. A compound of claim 2 wherein R is chloro.
5. A compound of claim 1 wherein n is one.
6. A compound of claim 1 wherein n is two.
7. A compound of claim 1 wherein $R_1$ and $R_4$ each is methyl.
8. A compound of claim 7 wherein R is fluoro and n is one.
9. A compound of claim 1 wherein $A^-$ is a hydrosulfate anion.
10. A compound of claim 1, said compound being 3-(3-fluorophenyl)-1,4-dimethyl-1,2,4-triazolium hydrosulfate.
11. A compound of claim 1, said compound being 3-(2-fluorophenyl)-1,4-dimethyl-1,2,4-triazolium hydrosulfate.
12. A compound of claim 1, said compound being 3-(2,6-difluorophenyl)-1,4-dimethyl-1,2,4-triazolium hydrosulfate.
13. A compound of claim 1, said compound being 3-(4-chlorophenyl)-1,4-dimethyl-1,2,4-triazolium hydrosulfate.
14. A compound of claim 1, said compound being 3-(4-bromophenyl)-1,4-dimethyl-1,2,4-triazolium hydrosulfate.
15. A compound of claim 1, said compound being 3-(3-fluoro-2-methoxyphenyl)-1,4-dimethyl-1,2,4-triazolium hydrosulfate.
16. A method for the treatment of depression which comprises administering to a patient in need thereof an effective dose of a compound of the formula

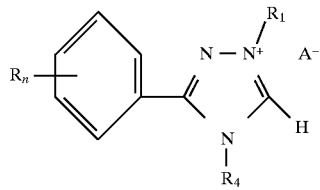

wherein

R is halogen, trifluoromethyl, $C_{1-4}$ lower alkyl or $C_{1-4}$ lower alkoxy;

n is zero, 1 or 2;

$R_1$ and $R_4$ independently represent $C_{1-3}$ lower alkyl;

and $A^-$ represents a pharmaceutically acceptable anion.

17. A method according to claim 16 wherein R is halogen.
18. A method according to claim 17 wherein R is fluoro.
19. A method according to claim 17 wherein R is chloro.
20. A method according to claim 16 wherein n is one.
21. A method according to claim 16 wherein n is two.
22. A method according to claim 16 wherein $R_1$ and $R_4$ each are methyl.
23. A method according to claim 22 wherein R is fluoro and n is one.
24. A method according to claim 16 wherein $A^-$ is a hydrosulfate anion.
25. A method according to claim 16, said compound being 3-(3-fluorophenyl)-1,4-dimethyl-1,2,4-triazolium hydrosulfate.
26. A method according to claim 16, said compound being 3-(2-fluorophenyl)-1,4-dimethyl-1,2,4-triazolium hydrosulfate.
27. A method according to claim 16, said compound being 3-(2,6-difluorophenyl)-1,4-dimethyl-1,2,4-triazolium hydrosulfate.
28. A method according to claim 16, said compound being 3-(4-chlorophenyl)-1,4-dimethyl-1,2,4-triazolium hydrosulfate.
29. A method according to claim 16, said compound being 3-(4-bromophenyl)-1,4-dimethyl-1,2,4-triazolium hydrosulfate.
30. A method according to claim 16, said compound being 3-(3-fluoro-2-methoxyphenyl)-1,4-dimethyl-1,2,4-triazolium hydrosulfate.
31. A pharmaceutical composition which comprises a compound of the formula

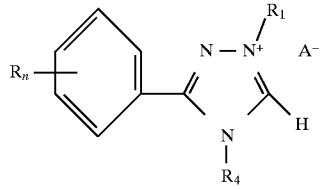

wherein

R is halogen, trifluoromethyl, $C_{1-4}$ lower alkyl or $C_{1-4}$ lower alkoxy;

n is zero, 1 or 2;

$R_1$ and $R_4$ independently represent $C_{1-3}$ lower alkyl;

and $A^-$ represents a pharmaceutically acceptable anion; and a pharmaceutically acceptable carrier.

32. A composition according to claim 31 wherein R is halogen.
33. A composition according to claim 32 wherein R is fluoro.

34. A composition according to claim 32 wherein R is chloro.

35. A composition according to claim 31 wherein n is one.

36. A composition according to claim 31 wherein n is two.

37. A composition according claim 31 wherein $R_1$ and $R_4$ each are methyl.

38. A composition according to claim 37 wherein R is fluoro and n is one.

39. A composition according to claim 30 wherein $A^-$ is a hydrosulfate anion.

40. A composition according to claim 30, said compound being 3-(3-fluorophenyl)-1,4-dimethyl-1,2,4-triazolium hydrosulfate.

41. A composition according to claim 30, said compound being 3-(2-fluorophenyl)-1,4-dimethyl-1,2,4-triazolium hydrosulfate.

42. A composition according to claim 30, said compound being 3-(2,6-difluorophenyl)-1,4-dimethyl-1,2,4-triazolium hydrosulfate.

43. A composition according to claim 30, said compound being 3-(4-chlorophenyl)-1,4-dimethyl-1,2,4-triazolium hydrosulfate.

44. A composition according to claim 30, said compound being 3-(4-bromophenyl)-1,4-dimethyl-1,2,4-triazolium hydrosulfate.

45. A composition according to claim 30, said compound being 3-(3-fluoro-2-methoxyphenyl)-1,4-dimethyl-1,2,4-triazolium hydrosulfate.

* * * * *